United States Patent
Park et al.

(10) Patent No.: US 8,927,116 B2
(45) Date of Patent: Jan. 6, 2015

(54) ORGANIC MATERIAL, FILM COMPRISING THE SAME AND ELECTRIC DEVICE COMPRISING THE FILM

(75) Inventors: Jong-jin Park, Yongin-si (KR); Kwang-hee Lee, Suwon-si (KR); Xavier Bulliard, Yongin-si (KR); Yun-hyuk Choi, Seoul (KR); Tae-gwan Park, Daejeon (KR)

(73) Assignees: Samsung Electronics Co., Ltd. (KR); Korea Advanced Institute of Science and Technology (KR)

( * ) Notice: Subject to any disclaimer, the term of this patent is extended or adjusted under 35 U.S.C. 154(b) by 978 days.

(21) Appl. No.: 12/476,664

(22) Filed: Jun. 2, 2009

(65) Prior Publication Data
US 2010/0117522 A1     May 13, 2010

(30) Foreign Application Priority Data
Nov. 13, 2008 (KR) .................. 10-2008-0112871

(51) Int. Cl.
| H01J 1/63 | (2006.01) |
|---|---|
| C08F 136/20 | (2006.01) |
| C07H 7/04 | (2006.01) |
| B32B 15/088 | (2006.01) |
| B32B 27/06 | (2006.01) |
| C07H 15/18 | (2006.01) |
| H01L 51/44 | (2006.01) |
| H01L 51/52 | (2006.01) |

(52) U.S. Cl.
CPC .............. *C07H 15/18* (2013.01); *H01L 51/448* (2013.01); *H01L 51/5237* (2013.01)
USPC ..... 428/690; 428/458; 428/477.7; 525/328.3; 536/53

(58) Field of Classification Search
None
See application file for complete search history.

(56) References Cited

U.S. PATENT DOCUMENTS

| 7,713,629 B2 * | 5/2010 | Schlenoff ...................... 428/421 |
|---|---|---|
| 2002/0120333 A1 | 8/2002 | Keogh et al. |
| 2004/0119400 A1 * | 6/2004 | Takahashi et al. ............ 313/504 |
| 2006/0156954 A1 | 7/2006 | Li et al. |
| 2007/0241675 A1 * | 10/2007 | Kim et al. ...................... 313/506 |
| 2009/0123652 A1 * | 5/2009 | Messersmith et al. ........ 427/352 |

FOREIGN PATENT DOCUMENTS

| JP | 56161537 A | 12/1981 |
|---|---|---|
| JP | 61203131 A | 9/1986 |
| KR | 1020010034195 A | 4/2001 |
| WO | 2005056708 A2 | 6/2005 |

OTHER PUBLICATIONS

R. Bitton et al., "Novel Biomimetic Adhesives Based on Algae Glue," Macromolecular Bioscience, 2008, vol. 8, pp. 393-400.
A.K. Geim et al., "Microfabricated adhesive mimicking gecko foot-hair," Nature Materials, vol. 2, Jul. 2003, pp. 461-463.
H. Lee et al., "A reversible wet/dry adhesive inspired by mussels and geckos," Nature, vol. 448, Jul. 19, 2007, pp. 338-342.

(Continued)

*Primary Examiner* — J. L. Yang
(74) *Attorney, Agent, or Firm* — Cantor Colburn LLP

(57) ABSTRACT

An organic material including a hydrophilic polymer and an organic moiety having a hydroxyl substituted $C_6$-$C_{14}$ aromatic functional group, the organic moiety binding to an end or a side of the hydrophilic polymer.

22 Claims, 6 Drawing Sheets

(56) References Cited

OTHER PUBLICATIONS

H. Lee et al., "Mussel-Inspired Surface Chemistry for Multifunctional Coatings," Science, vol. 318, Oct. 19, 2007, pp. 426-430.

S. Sethi et al., "Gecko-Inspired Carbon Nanotube-Based Self-Cleaning Adhesives," Nano Letters, 2008, vol. 8, No. 3, pp. 822,825.

Japanese Office Action for Japanese Patent Application No. 2009-259534 dated Nov. 5, 2013 with English Translation.

Ogawa et al., "Effect of Molecular Weight on Adhesion of Steel Plates with Polypropylene Sheet", J. Soc. Mat. Sci., Japan, vol. 41, No. 461, Feb. 1992, pp. 195-201.

* cited by examiner

ORGANIC MATERIAL, FILM COMPRISING THE SAME AND ELECTRIC DEVICE COMPRISING THE FILM

CROSS-REFERENCE TO RELATED APPLICATION

This application claims priority to Korean Patent Application No. 10-2008-0112871, filed on Nov. 13, 2008, and all the benefits accruing therefrom under 35 U.S.C. §119, the contents of which in its entirety are herein incorporated by reference.

BACKGROUND

1. Field

One or more embodiments relate to an organic material, a film including the same and an electric device including the film.

2. Description of the Related Art

An electric apparatus, such as an organic light emitting device, a plasma display panel, a field emission device or a thin film transistor can include films, which are patterned and stacked.

In an electric apparatus, an inorganic film can be formed on an organic film. Due to a difference between a surface energy of the organic film and a surface energy of the inorganic film, and a difference in other properties at the interface between the organic film and the inorganic film, an interfacial adhesive force between the organic film and the inorganic film can be lower than an interfacial adhesive force between an organic film and another organic film or an interfacial adhesive force between an inorganic film and another inorganic film. Insufficient interfacial adhesive force can reduce durability of an electric apparatus.

Accordingly, to improve durability of an electric apparatus, it is desirable to improve an interfacial adhesive force between an organic film and an inorganic film.

SUMMARY

One or more embodiments include an organic material having excellent adhesive properties.

One or more embodiments include a film including an organic film and an inorganic film, wherein an interfacial adhesive force between the organic film and the inorganic film is enhanced.

One or more embodiments include an electric device including a substrate and a conductive layer including an inorganic material and an organic film having adhesive properties interposed between the substrate and the conductive layer.

One or more embodiments include an electric apparatus including a thin film encapsulation layer, wherein the thin film encapsulation layer includes an organic film and an inorganic film and an interfacial adhesive force between the organic film and the inorganic film is enhanced.

Additional aspects are set forth in the description which follows.

To achieve the above and/or other aspects, features or advantages, an embodiment includes an organic material including: a hydrophilic polymer; and an organic moiety having a hydroxyl substituted $C_6$-$C_{14}$ aromatic functional group, the organic moiety binding to an end or a side of the hydrophilic polymer.

To achieve the above and/or other aspects, features or advantages, an embodiment includes a film including a double-layer system including an organic film and an inorganic film, wherein the organic film includes an organic material, the organic material including a hydrophilic polymer; and an organic moiety having a hydroxyl substituted $C_6$-$C_{14}$ aromatic functional group, the organic moiety binding to an end or a side of the hydrophilic polymer; and the inorganic film is disposed on the organic film and contacts a surface of the organic film.

Also disclosed is an electric device including an electrode or an interconnection line, the electrode or the interconnection line including the film.

To achieve the above and/or other aspects, features or advantages, one or more embodiments may include an electric device including: a substrate; a conductive layer including a metal, a metal oxide, or a combination of the metal and the metal oxide; and an organic film including an organic material, the organic material including: a hydrophilic polymer; and an organic moiety having a hydroxyl substituted $C_6$-$C_{14}$ aromatic functional group, the organic moiety binding to an end or a side of the hydrophilic polymer, wherein the organic film is interposed between the substrate and the conductive layer.

To achieve the above and/or other aspects, one or more embodiments may include an electric apparatus including: a device substrate including at least one electric device; and a thin film encapsulation layer covering the electric device, wherein the thin film encapsulation layer includes a double-layer system including an organic film and an inorganic film, the inorganic film disposed on the organic film and contacting a surface of the organic film, and the organic film including an organic material, the organic material including: a hydrophilic polymer; and an organic moiety having a hydroxyl substituted $C_6$-$C_{14}$ aromatic functional group, the organic moiety binding to an end or a side of the hydrophilic polymer.

BRIEF DESCRIPTION OF THE DRAWINGS

These and/or other aspects are apparent and can be more readily appreciated from the following description of the embodiments, taken in conjunction with the accompanying drawings in which.

DETAILED DESCRIPTION

Figure 1:
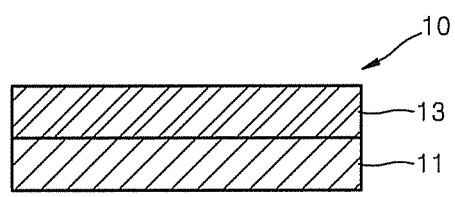
FIG. 1 is a schematic sectional view showing an exemplary embodiment of a film.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects, advantages and features of the disclosed embodiments.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

It will be understood that, although the terms first, second, third, etc., can be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the exemplary embodiments of the invention.

Spatially relative terms, such as "below," "lower," "upper" and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device can be otherwise oriented (rotated 90 degrees or at other orientations) and the spatially relative descriptors used herein interpreted accordingly.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation can result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

The term "hydroxyl substituted," as used herein, means that any one or more hydrogens on the designated atom or group are replaced with a hydroxyl group, provided that the designated atom's normal valence is not exceeded.

An organic material according to an embodiment includes a hydrophilic polymer and an organic moiety. The organic moiety includes a hydroxyl substituted $C_6$-$C_{14}$ aromatic functional group, the organic moiety binding to an end or a side of the hydrophilic polymer.

The hydrophilic polymer may comprise a polymer having polarity and an affinity with a polar solvent, such as water, alcohol, or the like, or a combination comprising at least one of the foregoing polar solvents. In an embodiment the hydrophilic polymer is soluble in the polar solvent.

Exemplary hydrophilic polymers include a polyvinyl alcohol, a polyvinyl pyrrolidone, a cellulose-based polymer, an acryl-based polymer, a polyethylene oxide, a polyester, a polyurethane, a polyethylene, gelatin, a hyaluronic acid, a polypropylene, a polystyrene, a copolymer having a quaternary ammonium species, or the like or a combination comprising at least one of the foregoing polymers. However, the hydrophilic polymer is not limited to the foregoing materials.

Exemplary hydrophilic polymers also include polyethyleneimine ("PEI"), a hyaluronic acid, polyhydroxyethyl methacrylate ("PHEMA"), polyacrylamide ("PAAM"), poly(methacrylic acid) ("PMAA"), polymaleic anhydride ("PMAH"), polyvinyl alcohol ("PVA"), polyethylene oxide ("PEO"), polyvinyl pyrrolidone ("PNVP"), polyglycolic acid ("PGA"), polylactic-glycolic acid ("PLGA"), polyurethane ("PU"), polyethylene ("PE"), polypropylene ("PP"), polyvinylchloride ("PVC"), polyester ("PET"), polyvinyl pyridine, cellulose acetate, polyacrylonitrile, polyacrylamide, polyethylene glycol, polyacrylate, polymethacrylate, polystyrene sulfonic acid ("PSSA"), polystyrene sulfonate, polyallyl sulfonic acid, polyvinyl sulfonate, polyallylamine hydrochloride, poly(2-(methyl)acrylamido-2-methylpropane sulfonic acid), poly(diallyldimethylammonium chloride), derivatives of the foregoing, or the like or a combination comprising at least one of the foregoing.

A weight average molecular weight of the hydrophilic polymer may vary according to the application of an organic film including the organic material. In an embodiment, a weight average molecular weight is between about 100 Daltons and about 100,000 Daltons, specifically between about 250 Daltons and about 10,000 Daltons, more specifically between about 500 Daltons and about 5,000 Daltons.

The hydroxyl substituted $C_6$-$C_{14}$ aromatic functional group may enhance an adhesive force between the organic film including the organic material and a neighboring film, and can control a surface roughness of an inorganic film disposed on the organic film.

The hydroxyl substituted $C_6$-$C_{14}$ aromatic functional group may be derived from a phenyl group, a naphthyl group, an anthryl group, or the like or a combination comprising at least one of the foregoing groups, but is not limited thereto.

The hydroxyl substituted $C_6$-$C_{14}$ aromatic functional group includes a hydroxyl group. Thus, in an embodiment, a hydrogen atom of the $C_6$-$C_{14}$ aromatic functional group is substituted with a hydroxyl group. The hydroxyl group enhances an adhesive force between the organic film and a neighboring film, such as an inorganic film.

The hydroxyl substituted $C_6$-$C_{14}$ aromatic functional group may be a catechol group, or the like, but is not limited thereto.

The organic moiety may be represented by Formula 1:

*-L-Ar—(OH)$_n$     Formula 1

In Formula 1, * denotes a binding site with the hydrophilic polymer.

In Formula 1, L may be a linking group comprising —C(=O)—(CH$_2$)$_a$— or —NH—(CH$_2$)$_b$—, where a and b are each independently an integer between 0 and about 50, specifically between about 1 and about 25, more specifically between about 2 and about 10. In an embodiment, a and b may each independently be an integer between 0 and about 5.

In Formula 1, Ar may be a $C_6$-$C_{14}$ aromatic functional group. In an embodiment, Ar may be a phenyl group, a naphthyl group, an anthryl group, or the like or a combination comprising at least one of the foregoing, but is not limited thereto.

In Formula 1, n denotes the number of sites at which a hydroxyl group is substituted in Ar and n may be between about 1 and about 13, specifically between about 2 and about 10, more specifically about 5. In an embodiment, n may be an integer between about 1 and about 5, but is not limited thereto.

In an embodiment, the organic moiety may be represented by Formulae 1a, 1b, 1c, or the like or a combination comprising at least one of the foregoing, but the structure of the organic moiety is not limited thereto:

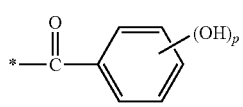

Formula 1a

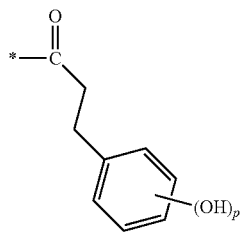

Formula 1b

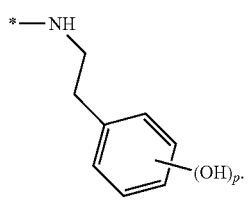

Formula 1c

In Formula 1a through 1c, * denotes a binding site with the hydrophilic polymer, and p is an integer between about 1 and about 5, specifically between about 2 and about 4, more specifically about 3.

In Formulae 2a through 2c below, the organic moiety, which can be represented by any one of Formulae 1a through 1c, or the like, can bind to a repeating unit of the hydrophilic polymer. The organic material may include a repeating unit represented by Formulae 2a through 2c, or the like or a combination thereof, but the structure of the organic material is not limited thereto:

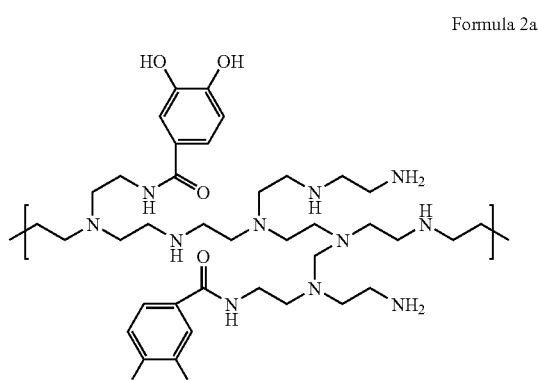

Formula 2a

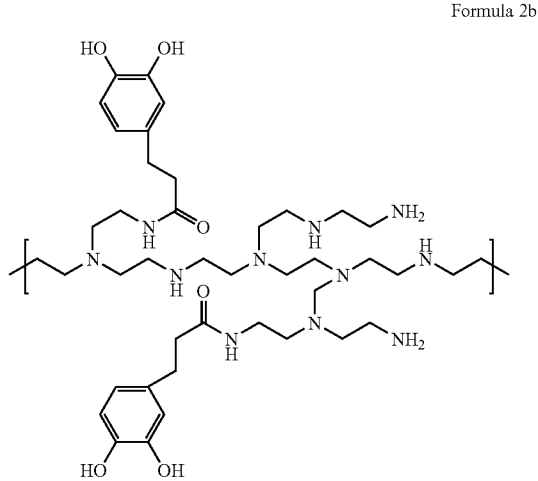

Formula 2b

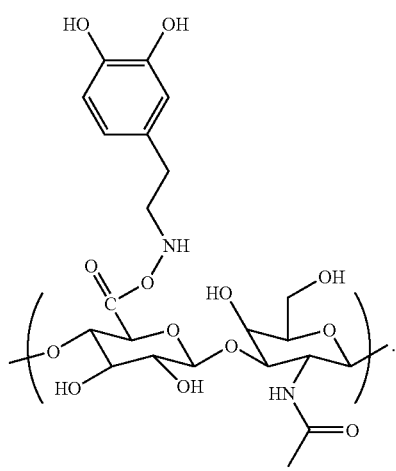

Formula 2c

In the organic material, the content of the repeating unit represented by Formulae 2a through 2c, or the like, may be controlled according to a grafting ratio or percent ("%") of the corresponding organic moiety.

A weight average molecular weight of the organic material may be determined according to the weight average molecular weight of the hydrophilic polymer and grafting ratio (or %) of the organic moiety.

FIG. 1 is a schematic sectional view showing an exemplary embodiment of a film 10. The film 10 includes a double-layer system, which includes an organic film 11 and an inorganic film 13 disposed on the organic film 11, wherein the inorganic film 13 contacts a surface of the organic film 11.

The organic film 11 includes an organic material, which includes a hydrophilic polymer and an organic moiety, wherein the organic moiety includes a hydroxyl substituted $C_6$-$C_{14}$ aromatic functional group bound to an end or a side of the hydrophilic polymer. Further description of the organic material is provided above.

The inorganic film 13 may include a metal such as an alkali metal, an alkali earth-based metal, a metalloid, an oxide of the metal, a nitride of the metal, or the like or a combination comprising at least one of the foregoing. In an embodiment, the inorganic film 13 includes a combination of at least one selected from the metal, the oxide of the metal and the nitride of the metal.

In an embodiment, the inorganic film 13 may include a metal such as B, Li, Na, K, Rb, Cs, Mg, Ca, Sr, Ba, Sc, Ti, Zr, Nb, Ta, Cr, Mo, W, Mn, Fe, Ru, Co, Ir, Ni, Pd, Pt, Cu, Ag, Au, Zn, Cd, Al, Ga, In, Ti, Si, Ge, Sn, Pb, Sb, Te, or the like, or an oxide of the metal, a nitride of the metal, or a combination comprising at least one selected from the metal, the oxide of the metal and the nitride of the metal. However, the inorganic film 13 may also include other materials.

As used herein, the term "a combination of at least one selected from the metal, the oxide of the metal and the nitride of the metal" refers to a material in which at least one selected from the metal, the oxide of the metal and the nitride of the metal is physically and/or chemically mixed. In an embodiment, the inorganic film 13 may have a multi-layer structure including at least one layer selected from a layer including the metal described above, a layer including the oxide of the metal and a layer including the nitride of the metal. In addition, the inorganic film 13 may be a simple mixture or alloy of at least one of the metal, the oxide of the metal or the nitride of the metal.

The inorganic film 13 may include a metal or an alloy of two or more types of metals, such as Mg, Al, Au, Pt, Mg:Ag, or the like; a metal oxide such as $Al_2O_3$, $SiO_2$, $B_2O_5$, $TiO_2$, $SnO_2$, $ZnO$, $In_2O_3$, $ZrO_2$, $GeO_2$, $AlSiO_x$, or the like; a metal oxide such as AlN, $Si_3N_4$, TiN, ZrN, BN, or the like; a metaloxynitride such as AlON, SiON, or AlSiON, or the like; or a combination of at least one material selected from a metal, a metal oxide, and a metal nitride, such as indium tin oxide ("ITO"), InSnO, silicon zinc oxide ("SZO"), SiZnO, indium zinc oxide ("IZO"), InZnO, indium zinc gallium oxide ("IZGO"), InGaZnO, or the like or a combination comprising at least one of the foregoing, but is not limited thereto.

In the film 10, the organic film 11 may have an adhesive force between about 5 grams force per 2 inches ("g·f/2 inch") and about 65 g·f/2 inch, specifically between about 6 g·f/2 inch and about 61 g·f/2 inch, more specifically between about 10 g·f/2 inch and about 40 g·f/2 inch, when measured according to ASTM D 903-49 or BS 5350. The adhesive force may be improved by the hydroxyl substituted $C_6$-$C_{14}$ aromatic functional group included in the organic film 11. The adhesive force may vary according to the content of the hydroxyl substituted $C_6$-$C_{14}$ aromatic functional group, specifically the grafting ratio of the organic moiety.

A surface roughness of the film 10, specifically a surface roughness of the inorganic film 13, may be between about 1 nanometer ("nm") and about 10 nm root-mean-square ("rms"). The surface roughness may be controlled by the hydroxyl substituted $C_6$-$C_{14}$ aromatic functional group included in the organic film 11. The surface roughness may be reduced as the number of the hydroxyl substituted $C_6$-$C_{14}$ aromatic functional groups, which is related to the grafting ratio of the organic moiety, is increased.

A water vapor transmission rate ("WVTR") of the film 10 may be between about 0.03 grams per square meter per day ("g/m²/day") and about 0.001 g/m²/day, specifically between about 0.01 g/m²/day and about 0.005 g/m²/day, more specifically about 0.08 g/m²/day at 37.8° C. in a relative humidity of about 100%. The foregoing WVTR is obtained when the thickness of the film 10 is about 210 nm. Although not wanting to be limited to a specific theory, it is believed that since the organic film 11 has excellent adhesive properties, an interfacial adhesive force between the organic film 11 and the inorganic film 13 contacting the surface of the organic film 11 is enhanced. Accordingly, a durability of the film 10 may be improved and thus water-permeation-prevention properties may also be improved.

The film 10 may have an optical transmittance between about 70% and about 99%, specifically between about 80% and about 90%, more specifically equal to or greater than about 85% in a visible region of wavelengths. In an embodiment, the film 10 may have an optical transmittance of equal to or greater than about 90%. Since the organic material disclosed above is can be transparent, when the inorganic film 13 comprises a transparent material or the inorganic film 13 has a thickness such that it is substantially transparent, the foregoing level of optical transmittance can be obtained. The film 10 has, in addition to the excellent water-permeation-prevention properties disclosed above, excellent optical transmittance properties. Accordingly, the film 10 may be, for example, a thin film encapsulation layer of a top emission-type organic light emitting device.

When the inorganic film 13 included in the film 10 comprises a conductive material, the inorganic film 13 may be an electrode or an interconnection line of an electric device, such as an organic light emitting device, a plasma display panel, a field emission device, a thin film transistor, a photovoltaic device, an integrated circuit, a pressure sensor, a chemical sensor, a bio sensor, a solar light device, or a device for illumination. When the inorganic film 13 is an electrode or an interconnection line of an electric device, the inorganic film 13 may be attached to a selected substrate by the organic film 11. In an embodiment, detachment of the inorganic film 13, which is an electrode or an interconnection line, may be reduced or effectively prevented.

In an embodiment, since an electric device may deteriorate due to external humidity and/or oxygen when not in use and/or when operated, the electric device can be encapsulated to protect it from external humidity and oxygen. Accordingly, by using the film 10 as a thin film encapsulation layer in an electric apparatus, an electric device included in the electric apparatus may be protected from humidity and/or oxygen.

Figure 2:
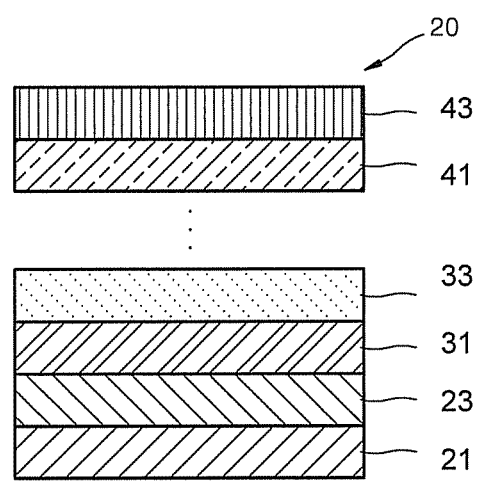
FIG. 2 is a schematic sectional view showing another exemplary embodiment of a film.

FIG. 2 is a schematic sectional view of a layered film 20 according to another embodiment.

The layered film 20 may include n double-layer systems. In an embodiment, n is between about 1 and about 100, specifically between about 2 and about 50, more specifically between about 4 and about 20. In an embodiment, n may be an integer of equal or greater than about 2. As shown in FIG. 2, the layered film 20 can comprise n double-layer systems. In an embodiment, the double layer systems may be sequentially deposited. A first double-layer system may include a first organic film 21 and a first inorganic film 23, and a second organic film 31 of a second double-layer system may be disposed on the first inorganic film 23. A second inorganic film 33 can be disposed on the second organic film 31. Thus the layered film 20 can comprise n double layer systems, and can comprise an $n^{th}$ organic film 41 and $n^{th}$ inorganic film 43. The first, second and $n^{th}$ organic films may be understood by referring to the description of the organic film 11 (see FIG. 1), and the first, second and $n^{th}$ inorganic films may be understood by referring to the inorganic film 13 (see FIG. 1), which is equally applied to the other double-layer systems. In the layered film 20, an organic material contained in each organic film may be equal to or different from each other, and materials for forming each inorganic film may be equal to or different from each other. Thus the material for each film can be selected independently.

In the layered film 20, adjacent layers may have excellent interfacial adhesive properties. For example, the second organic film is adjacent to and interposed between the first inorganic film and a second inorganic film. In an embodiment, since the second organic film includes the organic material disclosed above, an interfacial adhesive force between the second organic film and the first inorganic film is high and an interfacial adhesive force between the second organic film and the second inorganic film is also high, as can also be the case for each of the n organic films. Accordingly, the layered film 20 has excellent durability.

According to another embodiment, an electric device including a substrate, an organic film and a conductive layer is provided, wherein the organic film is interposed between the substrate and the conductive layer. The organic film includes an organic material including a hydrophilic polymer; and an organic moiety having a hydroxyl substituted $C_6$-$C_{14}$ aromatic functional group, the organic moiety binding to an end or a side of the hydrophilic polymer.

Figure 3:
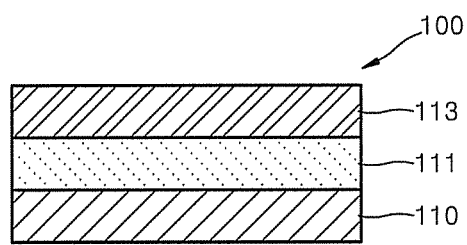
FIG. 3 is a schematic sectional view showing an exemplary embodiment of an electric device.

FIG. 3 is a schematic view showing an exemplary embodiment of an electric device 100. Referring to FIG. 3, the electric device 100 includes a substrate 110, an organic film 111 and a conductive layer 113.

The substrate 110 may comprise a commercially available material and can include a material having excellent smoothness, water resistance and ease of treatment properties. The substrate 110 may be a glass substrate, a plastic substrate, a metallic foil, or the like or a combination comprising at least one of the foregoing. If the plastic substrate or the metallic foil is used as the substrate 110, a flexible electric device can be obtained.

Exemplary materials for the plastic substrate include polyoxymethylene, polyvinylnaphthalene, polyetherketone, fluoropolymer, poly-alphamethyl styrene, polysulfone, polyphenylene oxide, polyetheramide, polyethersulfone, polyamideimide, polyimide, polyphthalamide, polycarbonate, polyarylate, polyethylenenaphthalate, polyethyleneterephthalate, or the like or a combination comprising at least one of the foregoing, but it is not limited thereto.

The conductive layer 113 may be an electrode or an interconnection line in the electric device. The conductive layer 113 may include a conductive material. In an embodiment, the conductive layer 113 may include a metal, a metal oxide or a combination of a metal and a metal oxide. A detailed description of the metal, the metal oxide and the combination of metal and metal oxide is provided above.

Since the organic film 111, including the organic material disclosed above, is interposed between the substrate 110 and the conductive layer 113, the conductive layer 113 may be strongly attached to the substrate 110. Accordingly, due to the organic film 111, the durability of the electric device 100 may be improved. A detailed description of the organic film 111 is provided above.

Figure 4:
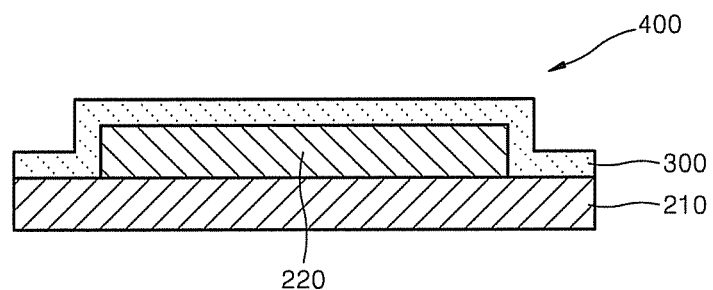
FIG. 4 is a schematic sectional view showing an exemplary embodiment of an electric apparatus.

FIG. 4 is a schematic sectional view showing an exemplary embodiment of an electric apparatus 400.

Referring to FIG. 4, the electric apparatus 400 includes a device substrate 210, an electric device 220 and a thin film encapsulation layer 300 covering the electric device 220. The thin film encapsulation layer 300 is a film including a double-layer system each including an organic film and an inorganic film contacting the organic film, wherein the organic layer includes an organic material including a hydrophilic polymer and at least one organic moiety having a hydroxyl substituted $C_6$-$C_{14}$ aromatic functional group, the organic moiety binding to an end or a side of the hydrophilic polymer. Further description of the film is provided by referring to FIGS. 1 and 2. Accordingly, the thin film encapsulation layer 300 has excellent durability due to excellent interfacial adhesive properties of the films constituting the thin film encapsulation layer 300. In addition, since the thin film encapsulation layer 300 has excellent optical transmittance and water-permeation-prevention properties, deterioration of the electric device 220 may be reduced or substantially prevented when the electric apparatus 400 is not in use and/or when operated.

The electric device 220 can be an organic light emitting device, a plasma display panel, a field emission device, a thin film transistor, a photovoltaic device, an integrated circuit, a pressure sensor, a chemical sensor, a bio sensor, a solar light device or a device for illumination. In an embodiment, the electric device 220 may be another type of device. In an embodiment, the electric device 220 may be an organic light emitting device ("OLED") including a pair of electrodes and an emission layer interposed between the electrodes. In an OLED, an organic material is interposed between electrodes of the organic light emitting device, which is a structure can be susceptible to deterioration caused by external humidity and/or oxygen. In an embodiment, the thin film encapsulation layer 300 reduces or effectively prevents permeation of external humidity and/or oxygen, and thus, a lifetime may be improved.

EXAMPLES

Preparation Example 1

Mixtures 1, 2 and 3 are prepared in the following manner.

Mixture 1: 1.54 milligrams ("mg") (10 millimoles ("mmol")) of 3,4-dihydroxy benzoic acid is dissolved in 10 milliliters ("ml") of dimethylformamide ("DMF").

Mixture 2: 2.5 mg (1.3 mmol) of 1-ethyl-3-3-dimethylaminopropyl carbodiimide hydrochloride ("EDC") is dissolved in 10 ml of methanol ("MeOH").

Mixture 3: 1 g of polyethyleneimine ("PEI"), having a weight average molecular weight ("Mw") of about 25,000, is dissolved in 20 ml of MeOH.

Mixtures 1 and 2 are mixed to activate 3,4-dihydroxy benzoic acid with EDC for 30 minutes. Then, Mixture 3 is added to the reaction product and mixed for 12 hours. The resultant product is precipitated twice with diethylether. The obtained precipitate is dissolved with deionized water (pH is adjusted to be about 5 or lower) and then dialyzed with respect to deionized water and lyophilized, thereby producing 8.5 grams ("g") of Sample 1 (PEI grafted with 3,4-dihydroxy benzoic acid, grafting ratio=1.80%, wherein grafting ratio refers to an area ratio of the peaks corresponding to H in the two hydroxyl OH groups of 3,4-dihydroxy benzoic acid when measured by $^1$H NMR).

Preparation Example 2

8.1 g of Sample 2 (PEI grafted with 3,4-dihydroxy benzoic acid, grafting ratio=1.34%) is prepared in the same manner as in Preparation Example 1, except that 1.14 mg of 3,4-dihydroxy benzoic acid is used to prepare Mixture 1.

Preparation Example 3

8.2 g of Sample 3 (PEI grafted with 3,4-dihydroxy benzoic acid, grafting ratio of 3,4-dihydroxy benzoic acid=0.73%) is prepared in the same manner as in Preparation Example 1, except that 0.62 mg of 3,4-dihydroxy benzoic acid is used to prepare Mixture 1.

Preparation Example 4

Mixtures 4, 5 and 6 are prepared in the following manner.
Mixture 4: 30.9 mg of hydrocaffeic acid is dissolved in 10 ml of DMF.
Mixture 5: 42.5 mg of EDC is dissolved in 30 ml of MeOH.
Mixture 6: 1 g of PEI (Mw=about 25,000) is dissolved in 30 ml of MeOH.

Mixtures 4 and 5 are mixed to activate hydrocaffeic acid with EDC for 30 minutes, and then Mixture 6 is added to the reaction product and mixed for 12 hours. The resultant product is precipitated twice with diethylether. The obtained precipitate is dissolved with deionized water (pH is adjusted to be about 5 or lower) and then dialyzed with respect to deionized water and lyophilized, thereby producing 8.7 g of Sample 4 (PEI grafted with hydrocaffeic acid, grafting ratio=15.28%, wherein grafting ratio refers to an area ratio of the peaks corresponding to H in the two hydroxyl OH groups of hydrocaffeic acid when measured by $^1$H NMR).

Preparation Example 5

8.3 g of Sample 5 (PEI grafted with hydrocaffeic acid, grafting ratio=7.47%) is prepared in the same manner as in Preparation Example 4, except that 15 mg of hydrocaffeic acid is used to prepare Mixture 4.

Preparation Example 6

7.6 g of Sample 6 (PEI grafted with hydrocaffeic acid, grafting ratio=21.03%) is prepared in the same manner as in Preparation Example 4, except that 15 mg of hydrocaffeic acid is used to prepare Mixture 4, and PEI (Mw=800), instead of PEI (Mw=25,000), is used to prepare Mixture 6.

Preparation Example 7

7.8 g of Sample 7 (PEI grafted with hydrocaffeic acid, grafting ratio=16.42%) is prepared in the same manner as in Preparation Example 4, except that 11 mg of hydrocaffeic acid is used to prepare Mixture 4, and PEI (Mw=800), instead of PEI (Mw=25,000), is used to prepare Mixture 6.

Preparation Example 8

Mixtures 7, 8 and 9 are prepared in the following manner.
Mixture 7: 1.8 mg (10 mmol) of dopamine hydrochloride is dissolved in 7 ml of DMF.
Mixture 8: 2.47 mg (13 mmol) of EDC is dissolved in 35 ml of MeOH.
Mixture 9: 0.5 g of hyaluronic acid (Mw=about 3,000) is dissolved in 30 ml MeOH.

Mixtures 7 and 8 are mixed to activate dopamine hydrochloride with EDC for 30 minutes, and then Mixture 9 is added to the reaction product and mixed for 12 hours. The resultant product is precipitated twice with diethylether. The obtained precipitate is dissolved with deionized water (pH is adjusted to be about 5 or lower) and then dialyzed with respect to deionized water and lyophilized, thereby producing 0.37 g of Sample 8 (hyaluronic acid grafted with dopamine, grafting ratio of dopamine=13.5%, wherein grafting ratio of dopamine refers to an area ratio of the peaks corresponding to H in the two hydroxyl OH groups of dopamine when measured by $^1$H NMR).

Evaluation Example 1

Adhesive Force Test

Adhesive forces of Samples 1 through 7 are measured according to a 180° peel test of ASTM D 903-49 or BS 5350:Part C11:1979. First, 0.1 g of Sample 1 is mixed with 5 g of H$_2$O and 0.5 g of ethanol to prepare a coating solution. The coating solution is coated to a size of 5 cm×30 cm on a polyethylene terephthalate ("PET") adhesive, which is coated on a substrate, and then dried at 140° C. for 5 minutes, thereby forming a Sample 1-containing film. Then, a force that is needed to separate a portion of the film from the PET and bend the potion at an angle of 180° is measured to evaluate an adhesive force of a Sample 1-containing film. The same test was performed on Sample 2 through 7. Compositions of coating solutions for respective Samples are illustrated in Table 1:

TABLE 1

| Sample No. | Amount of Sample (g) | Amount of H$_2$O (g) | Amount of EtOH (g) |
|---|---|---|---|
| 1 | 0.1 | 5 | 0.5 |
| 2 | 0.12 | 5 | 0.5 |
| 3 | 0.1 | 5 | 0.5 |
| 4 | 0.1 | 5 | 0.5 |
| 5 | 0.1 | 5 | 0.5 |
| 6 | 3.5 | 18 | 0.5 |
| 7 | 0.4 | 5 | 0.5 |

*Ethanol is referred to as "EtOH."

As a result, the adhesive force is a maximum of 61 g·f/2 inch, and a minimum of 6 g·f/2 inch.

Evaluation Example 2

Thermal Analysis Test

Thermo gravimetric analysis ("TGA") (N$_2$ atmosphere, temperature range of room temperature to 700° C. (10° C./min), Pan Type: Pt Pan in disposable Al Pan) on Samples 1 through 7 is performed by using a TA Instruments Q50001R instrument. The results are shown in Table 2:

TABLE 2

| Sample No. | Residual weight at 200° C. (%) | Residual weight at 600° C. (%) |
|---|---|---|
| 1 | 88.57 | 4.62 |
| 2 | 92.38 | 4.53 |
| 3 | 92.38 | 4.53 |
| 4 | 89.86 | 13.57 |
| 5 | 87.90 | 10.72 |
| 6 | 82.42 | 5.61 |
| 7 | 90.11 | 4.54 |

Example 1

A mixture including Sample 3 dissolved with 10 ml of a mixed solvent including (water/ethanol=1:1) is spin-coated on a polyethylene naphthalate ("PEN") substrate to a thickness of 10 μm, and then dried at 100° C. for 1 minute, thereby forming an organic film. Then, an inorganic film formed of $Al_2O_3$ having a thickness of 200 nm is formed on the organic film by non-reactive plasma vapor deposition ("PVD"). The resulting structure is referred to as Film 1.

Example 2

Film 2 is formed in the same manner as in Example 1, except that Sample 4 is used instead of Sample 3.

Example 3

Film 3 is formed in the same manner as in Example 1, except that Sample 7 is used instead of Sample 3.

Evaluation Example 3

Surface Morphology Test

Figure 5A:
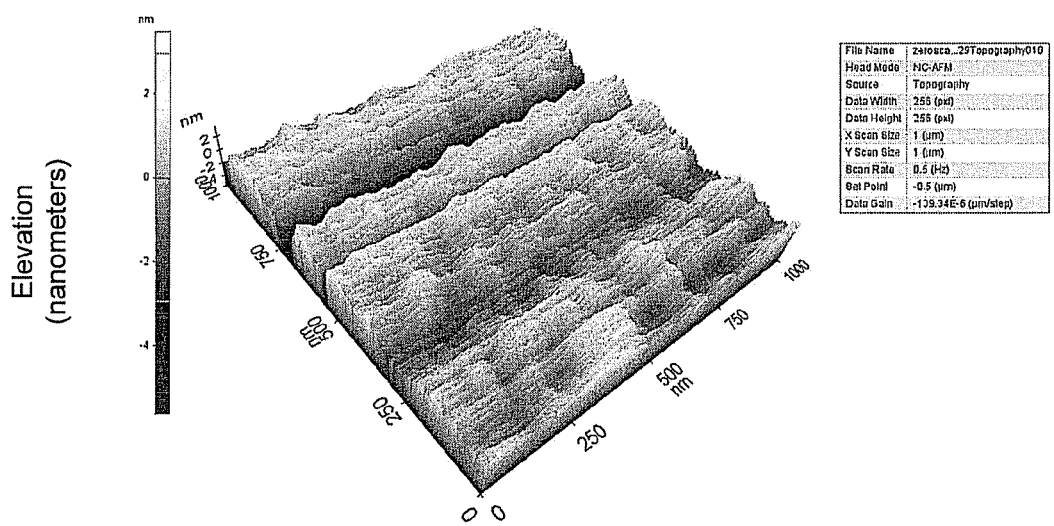
FIGS. 5A, 5B and 5C are atomic force microscope ("AFM") images showing surface morphologies of exemplary embodiments of films.
Figure 5B:
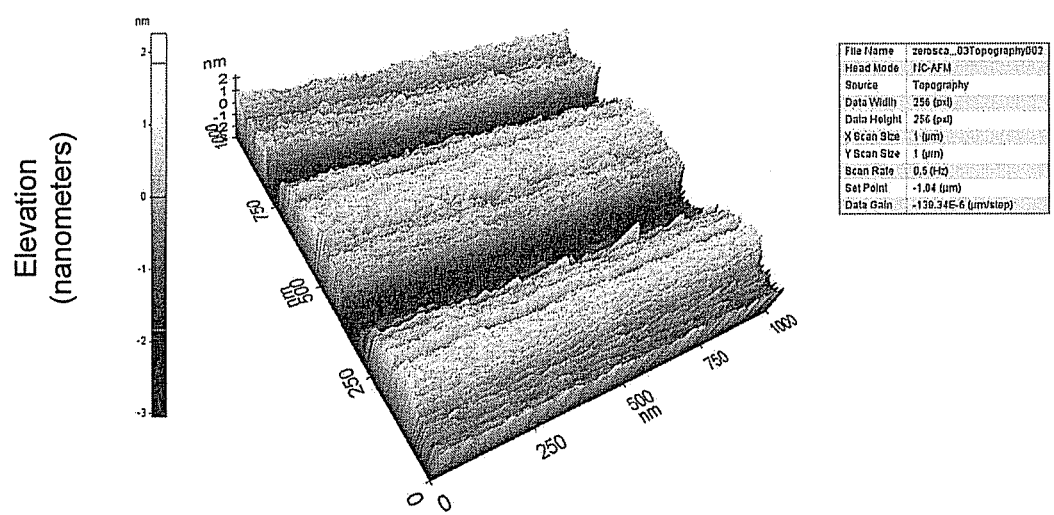
Figure 5C:
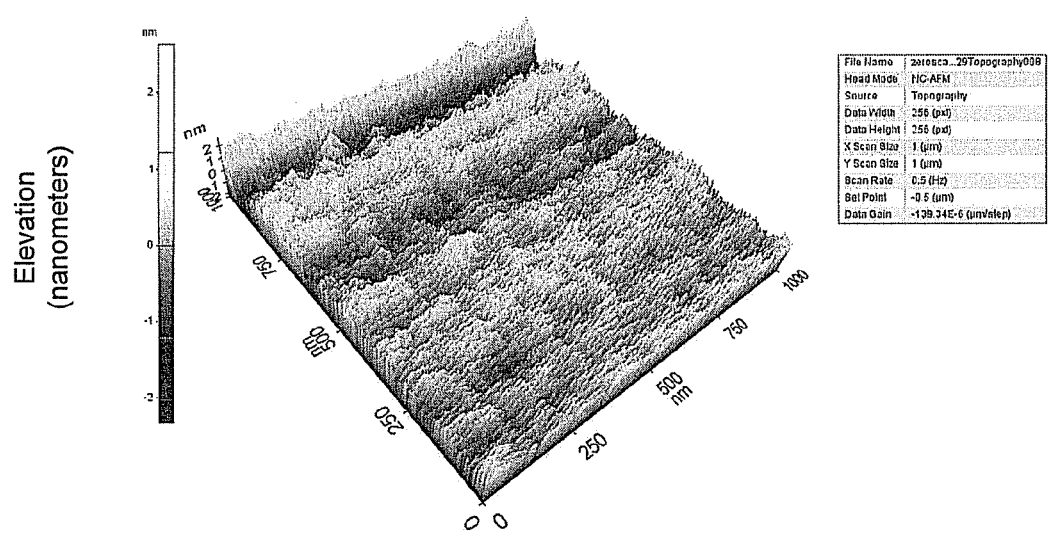

Surface morphologies of Films 1, 2 and 3 are identified by atomic force microscopy ("AFM"). Respective results are illustrated in FIGS. 5A, 5B and 5C. Referring to FIGS. 5A through 5C, as the amount of 3,4-dihydroxy benzoic acid contained in an organic film increases, the surface roughness of the inorganic film included in the organic film is reduced.

Example 4

Film 4 is formed in the same manner as in Example 1, except that the thickness of the Sample 3-containing organic film is selected to be 60 nm, and the inorganic film formed of $Al_2O_3$ is selected to be 150 nm.

Evaluation Example 4

Water Vapor Transmission Rate ("WVTR") Test

Figure 6:
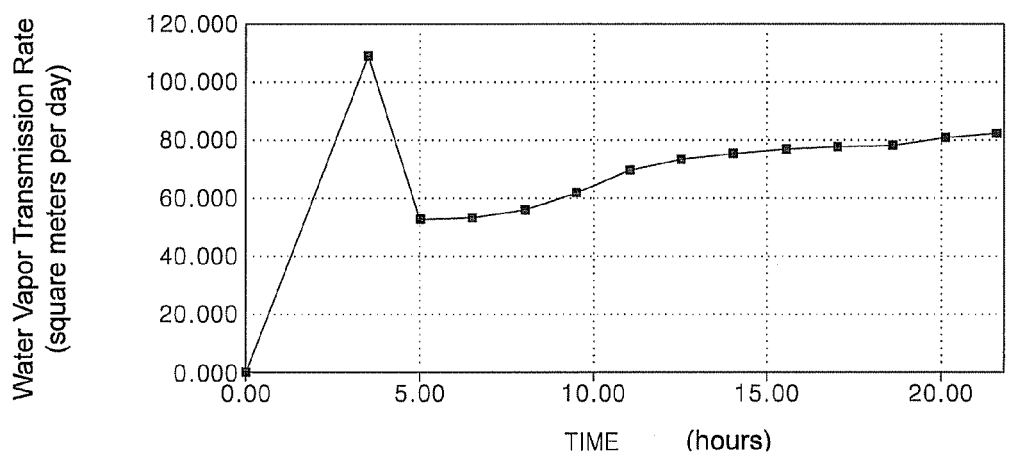
FIG. 6 is a graph illustrating water vapor transmission rate ("WVTR") with respect to time for an exemplary embodiment of a film.

The WVTR of Film 4 is measured by using a vapor permeation test instrument AQUATRAN model 1, (MOCON Co., USA) at 37.8° C. under 100% relative humidity. The WVTR of Film 4 is observed to be about 0.053 g/m²/day. WVTR test results on Film 4 are shown in FIG. 6 and Table 3.

TABLE 3

| Time | Cycle | TR/Event |
|---|---|---|
| 0:00 | Event | Condition |
| 2:00 | Event | Test |
| 3:30 | 1 | 109.4850 |
| 5:00 | 2 | 52.88736 |
| 6:30 | 3 | 53.57804 |
| 8:00 | 4 | 55.84842 |
| 9:30 | 5 | 61.86560 |
| 11:00 | 6 | 69.75210 |
| 12:30 | 7 | 73.37766 |
| 14:01 | 8 | 75.57224 |
| 15:32 | 9 | 76.98678 |
| 17:03 | 10 | 77.90554 |
| 18:34 | 11 | 78.47148 |
| 20:06 | 12 | 80.64676 |
| 21:37 | 13 | 82.28810 |
| 21:45 | Event | Complete |
| 21:45 | Event | Finished |

*TR refers to Transmission Rate.

Evaluation Example 4

Optical Transmittance Test

The optical transmittance of Film 4 is measured by using a CARY 5000 UV-VIS Spectrometer: (VARIAN Co). The optical transmittance is observed to be between about 85% and about 90% in the entire visible region.

As described above, according to the one or more of the above embodiments, when a film that includes an organic film and an inorganic film, wherein an interfacial adhesive force between the organic film and the inorganic film is high, an electric apparatus having high quality can be manufactured.

It should be understood that the exemplary embodiments described herein should be considered in a descriptive sense only and not for purposes of limitation. Descriptions of features or aspects within each embodiment should be considered as available for other advantages, features or aspects in other embodiments.

What is claimed is:
1. A film comprising: a double-layer system comprising an organic film and an inorganic film,
wherein the organic film comprises an organic material, the organic material comprising
a repeating unit represented by Formula 2a:

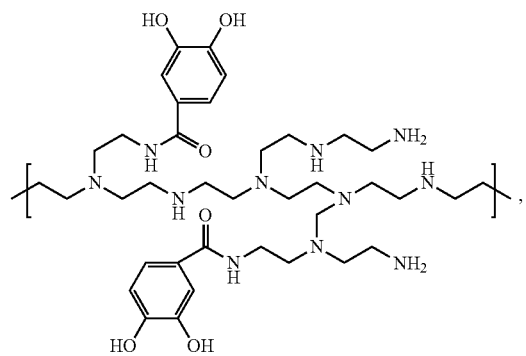

Formula 2a and
the inorganic film is disposed on the organic film and contacts a surface of the organic film.

2. The film of claim 1, wherein the inorganic film comprises a metal, an oxide of the metal, a nitride of the metal or a combination comprising at least one of the foregoing.

3. The film of claim 1, wherein an adhesive property of the organic film is between about 5 grams force per two inches and about 65 grams force per two inches when measured according to ASTM D 903-49 or BS 5350.

4. The film of claim 1, wherein a surface roughness of the inorganic film is between about 1 nanometer root-mean-square and about 10 nanometers root-mean-square.

5. The film of claim 1, having an optical transmittance equal to or greater than about 85 percent in a visible wavelength.

6. An electric device comprising an electrode or an interconnection line, the electrode or the interconnection line comprising the film of claim 1.

7. A thin film encapsulation layer, the thin film encapsulation layer comprising the film of claim 1.

8. An electric device comprising:
a substrate;
a conductive layer comprising a metal, a metal oxide or a combination of the metal and the metal oxide; and
an organic film comprising an organic material, the organic material comprising
a hydrophilic polymer; and
an organic moiety comprising a group represented by Formula 1a:

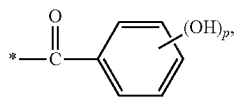

Formula 1a wherein p is 1 to 5, the organic moiety binding to an end or a side of the hydrophilic polymer,
wherein the organic film is interposed between the substrate and the conductive layer.

9. The electric device of claim 8, wherein the conductive layer is an electrode or an interconnection line.

10. An electric apparatus comprising:
a device substrate comprising an electric device; and
a thin film encapsulation layer covering the electric device,
wherein the thin film encapsulation layer comprises a double-layer system including an organic film and an inorganic film,
the inorganic film disposed on the organic film and contacting a surface of the organic film, and
the organic film comprising an organic material, the organic material comprising:
a hydrophilic polymer; and
an organic moiety comprising a group represented by Formula 1a:

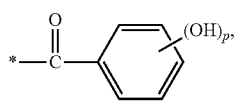

Formula 1a wherein p is 1 to 5, the organic moiety binding to an end or a side of the hydrophilic polymer.

11. The electric apparatus of claim 10, wherein the thin film encapsulation layer comprises at least two double-layer systems, the double layer systems sequentially deposited.

12. The electric apparatus of claim 10, wherein the electric device is an organic light emitting device.

13. The electric device of claim 8, wherein the organic moiety is derived from 3,4-dihydroxy benzoic acid.

14. The electric apparatus of claim 10, wherein the hydrophilic polymer is a polyvinyl alcohol, a polyvinyl pyrrolidone, a cellulose-based polymer, an acryl-based polymer, a polyethylene oxide, a polyester, a polyurethane, a polyethylene, gelatin, a hyaluronic acid, a polypropylene, a polystyrene, a copolymer having a quaternary ammonium species or a combination comprising at least one of the foregoing polymers.

15. The electric apparatus of claim 10, wherein the hydrophilic polymer is polyethyleneimine.

16. The electric apparatus of claim 10, wherein the organic moiety is derived from 3,4-dihydroxy benzoic acid.

17. The electric device of claim 8, wherein the metal oxide is $Al_2O_3$.

18. The film of claim 2, wherein the metal oxide is $Al_2O_3$.

19. The electric apparatus of claim 10, wherein the organic moiety is derived from 3,4-dihydroxy benzoic acid.

20. The electric device of claim 8, wherein the organic material comprises a repeating unit represented by Formula 2a:

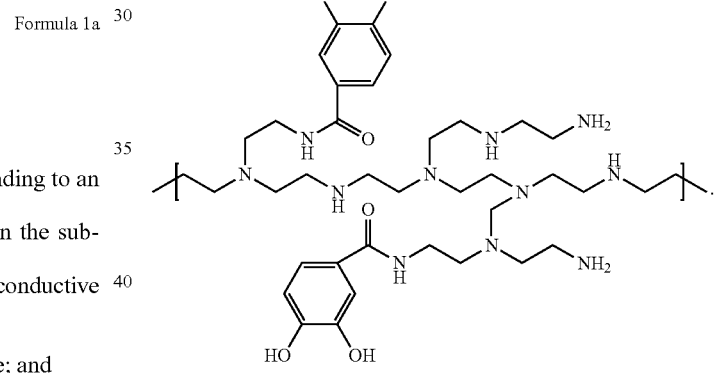

Formula 2a

21. The electric apparatus of claim 10, wherein the organic material comprises a repeating unit represented by Formula 2a:

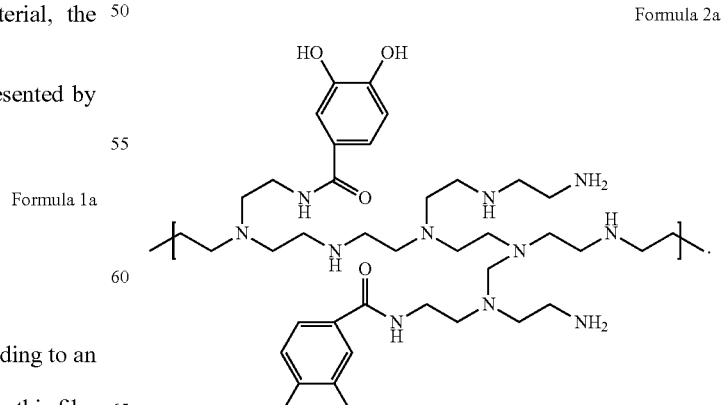

Formula 2a

22. An organic material comprising a repeating unit represented by Formula 2a:
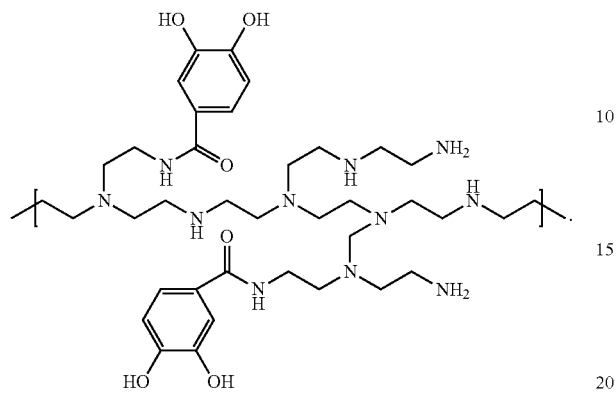
Formula 2a
* * * * *